(12) United States Patent
Tokuoka (10) Patent No.: US 11,231,352 B2
(45) Date of Patent: Jan. 25, 2022

(54) IMPACT TESTING MACHINE (71) Applicant: SHIMADZU CORPORATION, Kyoto (JP)

(72) Inventor: Nobuyuki Tokuoka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 140 days.

(21) Appl. No.: 16/821,065

(22) Filed: Mar. 17, 2020

(65) Prior Publication Data

US 2020/0309653 A1 Oct. 1, 2020

(30) Foreign Application Priority Data

Mar. 26, 2019 (JP) ............................. JP2019-058728

(51) Int. Cl.
*G01N 3/36* (2006.01)
*G01N 3/06* (2006.01)
(Continued)

(52) U.S. Cl.
CPC ............... *G01N 3/36* (2013.01); *G01N 3/068* (2013.01); *G01N 3/08* (2013.01); *G01N 3/30* (2013.01); *G01N 3/303* (2013.01); *G01N 33/442* (2013.01); *G01N 2203/001* (2013.01); *G01N 2203/0005* (2013.01); *G01N 2203/0017* (2013.01); *G01N 2203/0023* (2013.01); *G01N 2203/0039* (2013.01); *G01N 2203/0048* (2013.01);
(Continued)

(58) Field of Classification Search
CPC ............ G01N 3/36; G01N 3/068; G01N 3/08; G01N 3/303; G01N 3/30; G01N 2203/0048; G01N 2203/0017; G01N 2203/0005; G01N 2203/0023; G01N 2203/0641; G01N 2203/0682; G01N 2203/0647; G01N 2203/001; G01N 2203/0039; G01N 2203/0075; G01N 33/442

See application file for complete search history.

(56) References Cited

U.S. PATENT DOCUMENTS

2006/0005606 A1* 1/2006 Hatanaka ............... G01N 3/303
73/12.14

FOREIGN PATENT DOCUMENTS

JP 2004-069460 A 3/2004
JP 2005354209 A * 12/2005
(Continued)

*Primary Examiner* — Jonathan M Dunlap
(74) *Attorney, Agent, or Firm* — Sughrue Mion, PLLC (57) ABSTRACT

An impact testing machine is configured. The impact testing machine includes: a testing machine body that applies a load having a prescribed speed to a test piece and conducts a test; a controller that controls the testing machine body; a video camera that photographs the test piece; and a pulse generator. The controller includes: a detection signal capturing unit that captures a detection signal of the load in a prescribed measurement sampling period; and a synchronizing signal output unit that outputs a sampling synchronizing signal that is synchronized with the measurement sampling period. The pulse generator includes: a photographing instruction signal generator that generates a photographing instruction signal by multiplying or dividing the sampling synchronizing signal, and outputs the photographing instruction signal to the video camera. The photographing instruction signal issues a photographing instruction to the video camera.

4 Claims, 5 Drawing Sheets

(51) Int. Cl.
  *G01N 3/08*   (2006.01)
  *G01N 33/44*  (2006.01)
  *G01N 3/303*  (2006.01)
  *G01N 3/30*   (2006.01)

(52) U.S. Cl.
  CPC ............... *G01N 2203/0075* (2013.01); *G01N 2203/0641* (2013.01); *G01N 2203/0647* (2013.01); *G01N 2203/0682* (2013.01)

(56) References Cited

FOREIGN PATENT DOCUMENTS

JP   2012189321 A * 10/2012
WO  WO-2016192696 A1 * 12/2016 ............. G01N 3/068

* cited by examiner

IMPACT TESTING MACHINE

INCORPORATION BY REFERENCE

The present application claims priority under 35 U.S.C. § 119 to Japanese Patent Application No. 2019-058728 filed on Mar. 26, 2019. The content of the applications is incorporated herein by reference in its entirety.

BACKGROUND

Technical Field

The present invention relates to an impact testing machine.

Related Art

As an apparatus that conducts a test for investigating the mechanical characteristics or properties of a material, a material testing machine has conventionally been used widely in the industrial or academic field. Examples of a principal measurement value in the test include the magnitude of a load that deforms a test piece of a material and the displacement of the test piece, when the load is applied.

In addition, as one example of the material testing machine, an impact testing machine is known. The impact testing machine is a testing machine that applies a load (also referred to as an "impact force") to a test piece at a high speed (also referred to as "impact speed") of, for example, 5 m/sec or more so as to investigate the characteristics or properties of the test piece at the time of high-speed deformation (see, for example, JP 2004-69460 A). The impact testing machine is used in a test such as a high-speed tensile test or a puncture impact test, and data obtained in this test is utilized to analyze automobile collision, the fall of an electronic device, or the like that causes the high-speed deformation of a material.

SUMMARY

By providing a material testing machine with a video camera that photographs a deformation process of a test piece at a prescribed frame rate (also referred to as "photographing speed"), a captured image that records the deformation process can be obtained every time period that is equivalent to the reciprocal of the frame rate (hereinafter referred to as a "photographing sampling period"). Then, an amount of displacement or an amount of distortion (hereinafter referred to as a "deformation amount") of the test piece in the deformation process can be measured in a non-contact manner on the basis of respective captured images. In addition, a correspondence relationship between a load applied to the test piece and the deformation amount can be analyzed on the basis of a measurement result of the deformation amount.

However, in a case where a phase shift (in other words, a time difference) has occurred between a measurement sampling period in which the load is measured and the photographing sampling period, a load at a certain point in time is associated with a deformation amount based on a captured image that has been obtained at a point in time that has shifted from the certain point in time by a phase difference, and there is a problem in which the reliability of an analysis result deteriorates.

In particular, in the impact testing machine, in contrast to a general material testing machine that applies a static load, both a load applied to a test piece and a deformation amount of the test piece due to this load change at high speed. Therefore, an influence of a phase shift on the reliability of an analysis result is remarkable.

It is an object of the present invention to provide an impact testing machine that is capable of improving the reliability of an analysis result.

A first aspect of the present invention relates to an impact testing machine including: a testing machine body that applies a load having a prescribed speed to a test piece and conducts a test; a controller that controls the testing machine body; a video camera that photographs the test piece; and a pulse generator, in which the testing machine body includes: a detection signal capturing unit that captures a detection signal of the load in a measurement sampling period that has been prescribed; and a synchronizing signal output unit that outputs a sampling synchronizing signal that is synchronized with the measurement sampling period, and the pulse generator includes: a photographing instruction signal generator that generates a photographing instruction signal by multiplying or dividing the sampling synchronizing signal, and outputs the photographing instruction signal to the video camera, the photographing instruction signal issuing a photographing instruction to the video camera.

According to the present invention, a video camera performs a photographing operation in accordance with an input of a photographing instruction signal. Therefore, a phase shift between a measurement sampling period and a photographing sampling period of the video camera can be suppressed, and the reliability of an analysis result can be improved.

DETAILED DESCRIPTION

Embodiments of the present invention are described below with reference to the drawings. In the present embodiments, a high-speed tensile testing machine is described as an impact testing machine according to the present invention.

First Embodiment

Figure 1:
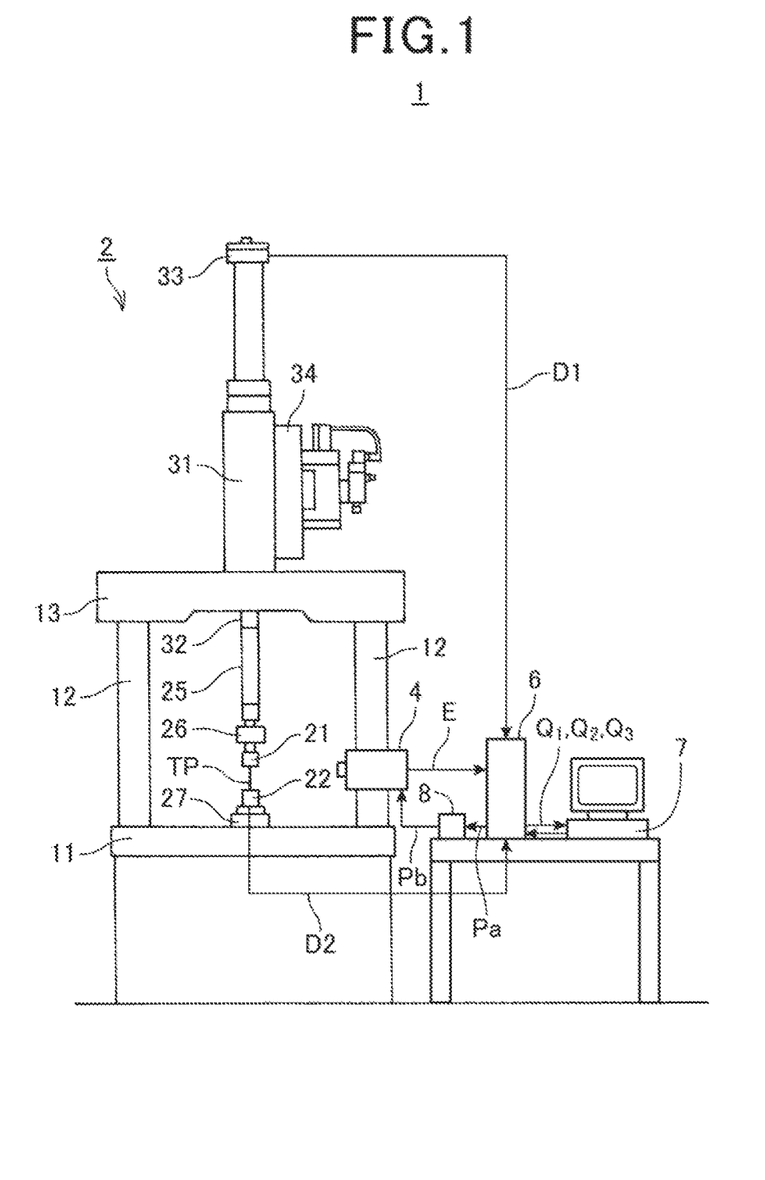
FIG. 1 is a diagram schematically illustrating a configuration of a high-speed tensile testing machine according to an embodiment of the present invention.

FIG. 1 is a diagram schematically illustrating a configuration of a high-speed tensile testing machine 1 according to the present embodiment.

The high-speed tensile testing machine 1 applies a tensile force (a load) to a test piece TP of a material of a test target at a prescribed impact speed so as to conduct a high-speed tensile test. The high-speed tensile testing machine 1 includes a testing machine body 2, a video camera 4, a controller 6, an analysis device 7, and a pulse generator 8. The impact speed is, for example, 5 m/sec or more, and is approximately 20 m/sec in the present embodiment. The test target is a variety of materials or industrial products, parts or members of the industrial products, or the like, and the test piece TP is prepared according to a prescribed standard for a material test.

The testing machine body 2 includes a table 11, a pair of supports 12 that are erected on the table 11, a cross yoke 13 that is bridged over the pair of supports 12, and a hydraulic cylinder 31 that is fixed to the cross yoke 13.

The hydraulic cylinder 31 configures a load mechanism that applies a tensile force to the test piece TP in the testing machine body 2. The hydraulic cylinder 31 operates due to hydraulic oil that is supplied via a servo valve 34 from a hydraulic source (not illustrated) that is disposed in the table.

An upper gripper 21 is connected to a piston rod 32 of the hydraulic cylinder 31 via an approach jig 25 and a joint 26. In contrast, a lower gripper 22 is connected to the table 11 via a load cell 27 serving as a force detector.

In the configuration described above, the testing machine body 2 pulls up the piston rod 32 at an impact speed of 5 m/sec or more (in the present embodiment, 20 m/sec), as described above. By doing this, a force that abruptly separates a pair of the upper gripper 21 and the lower gripper 22 from each other acts on the pair of the upper gripper 21 and the lower gripper 22, and this force acts, as a tensile force, on the test piece TP that is gripped by the pair of the upper gripper 21 and the lower gripper 22.

The testing machine body 2 is provided with a stroke sensor 33 and the load cell 27. The stroke sensor 33 outputs, to the controller 6, a stroke detection signal D1 according to the displacement of the load mechanism, i.e., an amount of movement of the piston rod 32. The load cell 27 serves as a force detector, and outputs, to the controller 6, a force detection signal D2 indicating a tensile force. The displacement of the load mechanism (the amount of movement of the piston rod 32) corresponds to a deformation amount of the test piece TP, and the deformation amount is obtained on the basis of the stroke detection signal D1 indicating the displacement.

The video camera 4 repeatedly performs an operation to photograph the test piece TP in synchronization with a photographing instruction signal Pb described later of the pulse generator 8, generates, in every photographing operation, a captured image E recording the test piece TP, and outputs the captured image E to the controller 6. Image processing is performed on respective captured images E by using, for example, the analysis device 7, so that the deformation amount of the test piece TP is measured. An appropriate publicly known technique is used in this image processing.

The controller 6 is a device that controls an operation of the testing machine body 2 so as to conduct a high-speed tensile test and that obtains time-series data Q1 of the stroke detection signal D1 indicating the deformation amount of the test piece TP, time-series data Q2 of the force detection signal D2 indicating the tensile force, and time-series data Q3 of the captured image E during the high-speed tensile test. The analysis device 7 that is configured, for example, by a personal computer or the like is connected to the controller 6 by wire or wirelessly. Each of the time-series data Q1, the time-series data Q2, and the time-series data Q3 is transmitted from the controller 6 to the analysis device 7 at an appropriate timing, and the analysis device 7 analyzes characteristics or properties relating to the high-speed deformation of the test piece TP on the basis of the time-series data Q1, the time-series data Q2, and the time-series data Q3. This analysis device 7 also functions as an input interface that sets, in the controller 6, a variety of setting parameters (such as impact speed) relating to the high-speed tensile test.

In a case where the analysis device 7 measures the deformation amount of the test piece TP on the basis of the time-series data Q3 of the captured image E, the time-series data Q1 of the stroke detection signal D1 does not always need to be output to the analysis device 7 in the testing machine body 2.

Figure 2:
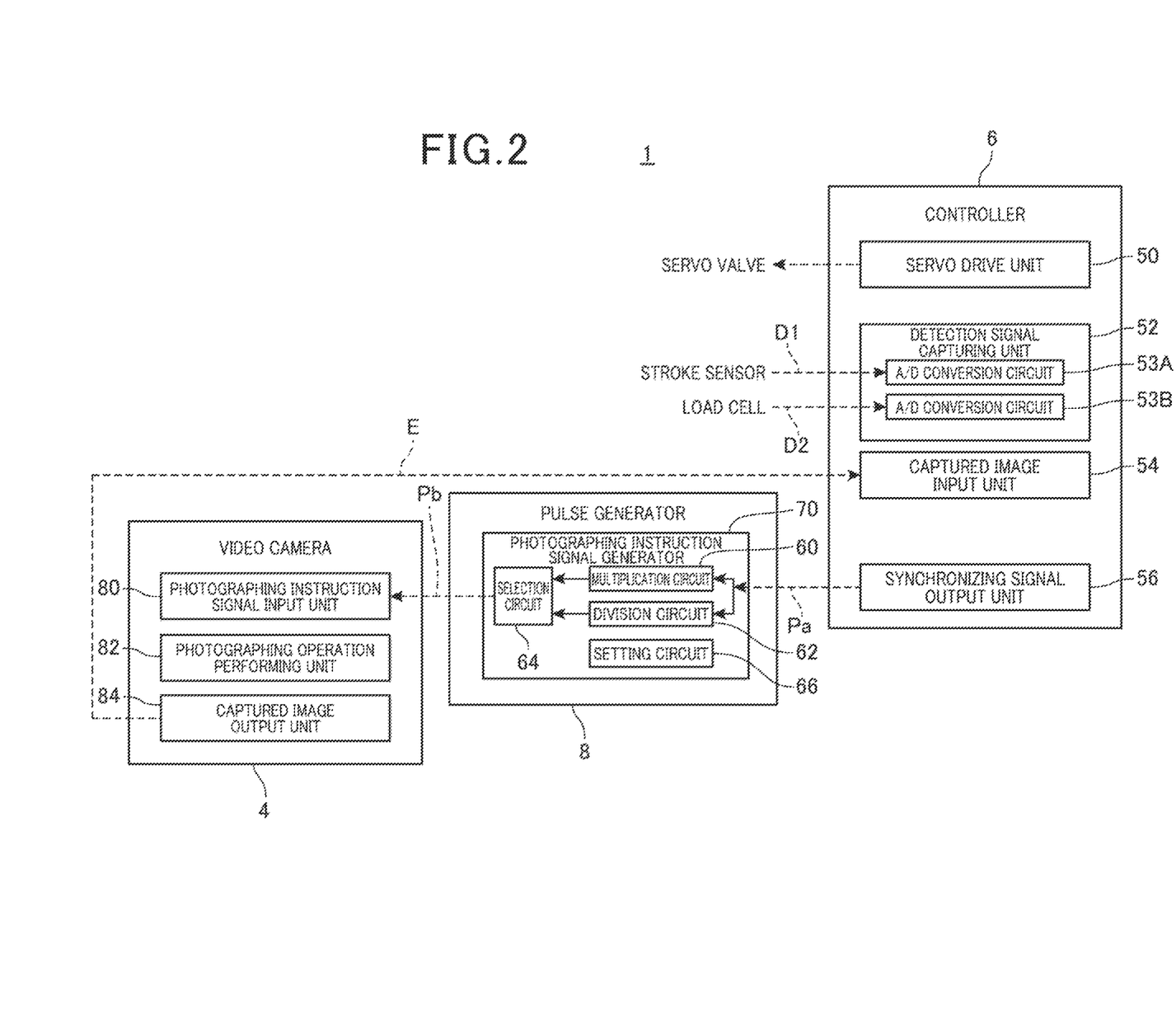
FIG. 2 is a diagram illustrating the functional configurations of a controller, a pulse generator, and a video camera.

FIG. 2 is a diagram illustrating the functional configurations of the controller 6, the pulse generator 8, and the video camera 4.

In the present embodiment, the controller 6 includes a servo drive unit 50, a detection signal capturing unit 52, a captured image input unit 54, and a synchronizing signal output unit 56, as illustrated in FIG. 2.

The controller 6 includes a computer that includes a processor such as a CPU or an MPU, a memory device such as a ROM or a RAM, a storage device such as an HDD or an SSD, an interface circuit for connection of sensors, peripheral equipment, or the like, and a communication device that performs communication with the analysis device 7. The processor executes a computer program (a testing machine control program) that is stored in the memory device or the storage device, so that the functions illustrated in FIG. 2 are implemented.

The servo drive unit 50 supplies a control signal to the servo valve 34 in such a way that the piston rod 32 is pulled up at a prescribed high speed, and causes the hydraulic cylinder 31 to operate.

The detection signal capturing unit 52 includes A/D conversion circuits 53A and 53B that sequentially capture the stroke detection signal D1 and the force detection signal D2, respectively, perform A/D conversion on the stroke detection signal D1 and the force detection signal D2, and perform an output. Outputs of these A/D conversion circuits 53A and 53B serve as the time-series data Q1 of the stroke detection signal D1 and the time-series data Q2 of the force detection signal D2.

These A/D conversion circuits 53A and 53B operate in synchronization with a common clock signal, and performs the capturing of the stroke detection signal D1 and the force detection signal D2 and the output of the time-series data Q1 of the stroke detection signal D1 and the time-series data Q2 of the force detection signal D2 in synchronization with each other in each prescribed measurement sampling period Tb. An appropriate clock circuit may be used as a generating source of such a clock signal, and a clock circuit that is included in the processor may be used, for example.

The measurement sampling period Tb has a value (the order of several MHz or more) that is greater than a value (in general, about several kHz) that is used in a normal material testing machine that applies a static load to the test piece TP, and a period that decreases as a setting value of impact speed increases is set, for example, by the processor. By doing this, even in a case where a higher impact speed is set and the test piece TP changes more abruptly, the stroke detection signal D1 and the force detection signal D2 can always be captured at a resolution sufficient with respect to an abrupt change, and a deformation amount and a tensile force can be measured.

The captured image input unit 54 includes an input terminal to which the captured image E of the video camera 4 is input. As described above, the video camera 4 sequentially generates the captured image E in synchronization with the photographing instruction signal Pb of the pulse generator 8, and each of the captured images E is input to the captured image input unit 54 at an appropriate timing. Then, the controller 6 transmits data in which the respective captured images E are arranged in a photographing order, as the time-series data Q3 of the captured image E to the analysis device 7.

The synchronizing signal output unit 56 outputs, to the pulse generator 8, a signal that is synchronized with the measurement sampling period Tb in the detection signal capturing unit 52 (hereinafter referred to as a "sampling synchronizing signal Pa"). This sampling synchronizing signal Pa is generated from the clock signal that is input to the A/D conversion circuits 53A and 53B.

The pulse generator 8 is a device that includes a photographing instruction signal generator 70 that outputs a photographing instruction signal Pb that issues a photographing instruction to the video camera 4, in accordance with the measurement sampling period Tb of the stroke detection signal D1 and the force detection signal D2 in the controller 6, so as to suppress a phase shift between a photographing sampling period Ta in the video camera 4 and the measurement sampling period Tb in the controller 6.

Specifically, the photographing instruction signal generator 70 includes a multiplication circuit 60 that outputs a multiplied signal obtained by multiplying the sampling synchronizing signal Pa, a division circuit 62 that outputs a divided signal obtained by dividing the sampling synchronizing signal Pa, a selection circuit 64 that selectively outputs either the multiplied signal or the divided signal as the photographing instruction signal Pb to the video camera 4, and a setting unit 66 that sets a multiplication number and a division number, as illustrated in FIG. 2.

The multiplication circuit 60 and the division circuit 62 are configured by using, for example, a PLL circuit.

In the selection circuit 64, which of the multiplied signal and the divided signal will be selected is set in advance. This selection is determined on the basis of the measurement sampling period Tb in the controller 6 and a photographing operation time period of the video camera 4.

The photographing operation time period is a time period required to perform a photographing operation of one frame, and is obtained according to the specifications of photographing speed. In general, as the data size of a captured image increases, the photographing operation time period also increases.

In a case where this photographing operation time period is longer than one period of the measurement sampling period Tb, the divided signal is selected as the photographing instruction signal Pb. In addition, in a case where the video camera 4 is a high-speed camera, the photographing operation time period is generally shorter than one period of the measurement sampling period Tb. In this case, if the photographing operation time period is less than or equal to 1/N (N is an integer of 2 or more) of one period of the measurement sampling period Tb, the multiplied signal is selected as the photographing instruction signal Pb.

In the setting unit 66, the multiplied signal of the measurement sampling period Tb; or a multiplication number or a division number that enables a photographing operation to be performed following the divided signal; is set on the basis of the photographing operation time period, and the multiplication number or the division number is input to the multiplication circuit 60 or the division circuit 62 that is described above. This setting may be performed manually.

Alternatively, a processor included in the pulse generator 8 may calculate the multiplication number or the division number on the basis of a photographing operation time period that has been input by a user, and this setting may be performed.

The video camera 4 includes a photographing instruction signal input unit 80 and a photographing operation performing unit 82, as illustrated in FIG. 2.

The photographing instruction signal input unit 80 includes an input terminal that receives an input of the photographing instruction signal Pb, and outputs the photographing instruction signal Pb to the photographing operation performing unit 82.

Every time the photographing instruction signal Pb is input, the photographing operation performing unit 82 performs a photographing operation to photograph the test piece TP so as to generate a captured image E of one frame, and stores the captured image E in a built-in memory device.

The captured image output unit 84 outputs a newly captured image E to the controller 6, every time the newly captured image E is stored in the memory device. Alternatively, the captured image output unit 84 outputs, to the controller 6, respective captured images E that have been stored in the memory device during one high-speed tensile test, every time the high-speed tensile test has been completed.

Figure 3:
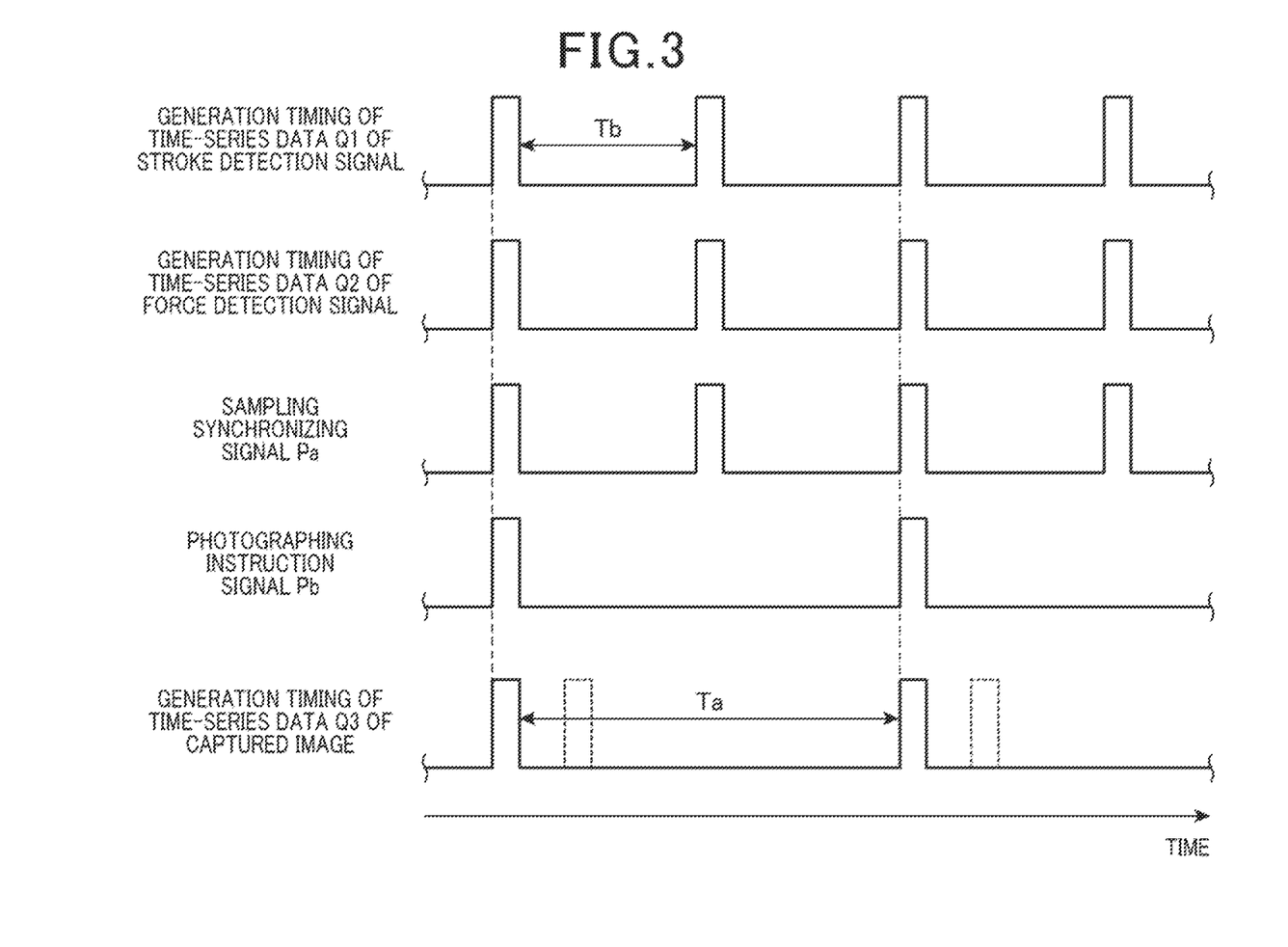
FIG. 3 is a timing chart illustrating a generation timing of each of time-series data of a stroke detection signal, time-series data of a force detection signal, and time-series data of a captured image, a sampling synchronizing signal, and a photographing instruction signal.

FIG. 3 is a timing chart illustrating a generation timing of each of the time-series data Q1 of the stroke detection signal D1, the time-series data Q2 of the force detection signal D2, and the time-series data Q3 of the captured image E, the sampling synchronizing signal Pa, and the photographing instruction signal Pb.

Both the time-series data Q1 of the stroke detection signal D1 and the time-series data Q2 of the force detection signal D2 are generated in each measurement sampling period Tb without almost no phase shift between the time-series data Q1 and the time-series data Q2 in the detection signal capturing unit 52, and a sampling synchronizing signal Pa that is synchronized with the time-series data Q1 and the time-series data Q2 is output to the pulse generator 8.

In the pulse generator 8, a multiplied signal or a divided signal of the sampling synchronizing signal Pa is sequentially output as the photographing instruction signal Pb, and the photographing instruction signal Pb is sequentially input to the video camera 4. Note that FIG. 3 illustrates a case where a divided signal obtained by performing ½ division on the sampling synchronizing signal Pa has been selected as the photographing instruction signal Pb.

The video camera 4 immediately performs a photographing operation of one frame by using an input of the photographing instruction signal Pb as a trigger so as to generate one captured image E. By doing this, a generation timing of the captured image E is always synchronized with a generation timing of the time-series data Q1 of the stroke detection signal D1 and the time-series data Q2 of the force detection signal D2. As a result, a phase shift from the measurement sampling period Tb, as indicated as a photographing sampling period Ta illustrated with a broken line in the drawing, can be sufficiently suppressed.

Figure 4:
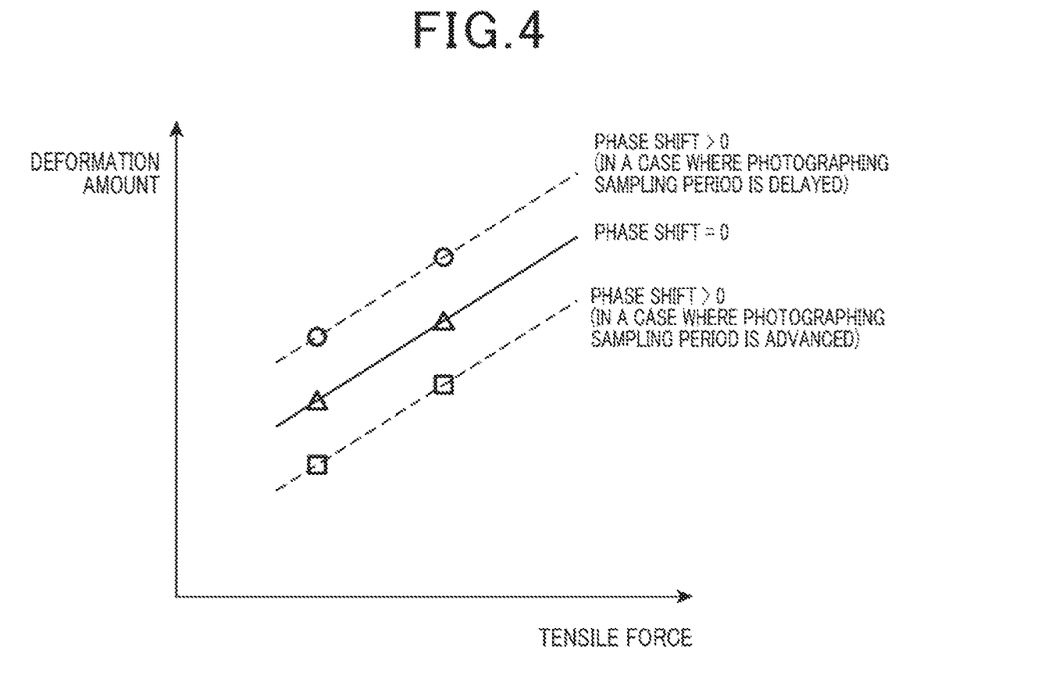
FIG. 4 is a diagram schematically illustrating an example of an analysis result obtained by analyzing the time-series data of the force detection signal and the time-series data of the captured image.

FIG. 4 is a diagram schematically illustrating an example of an analysis result obtained by analyzing the time-series data Q2 of the force detection signal D2 and the time-series data Q3 of the captured image E.

It is assumed that an analysis result has been obtained that indicates that a deformation amount obtained from the time-series data Q3 of the captured image E linearly changes with respect to a tensile force indicated by the time-series data Q2 of the force detection signal D2, as illustrated in this drawing.

In this case, when there is a phase shift between the photographing sampling period Ta and the measurement sampling period Tb, a value of the deformation amount increases or decreases in appearance in comparison with the case of no phase shift (a shift amount=zero) in accordance with an amount of the phase shift (a time difference) and a direction of the phase shift (a direction in which the photographing sampling period Ta is delayed or advanced), and the reliability of an analysis result deteriorates.

In contrast, in this high-speed tensile testing machine 1, a phase shift between the photographing sampling period Ta and the measurement sampling period Tb is sufficiently suppressed, and therefore an analysis result having high reliability can be obtained.

According to the present embodiment, the following effects are exhibited.

In the high-speed tensile testing machine 1 according to the present embodiment, the testing machine body 2 outputs a sampling synchronizing signal Pa that is synchronized with a prescribed measurement sampling period Tb serving as a period of the capturing of a force detection signal D2 indicating a tensile force, and the pulse generator 8 generates a photographing instruction signal Pb by multiplying or dividing this sampling synchronizing signal Pa, and outputs the photographing instruction signal Pb to the video camera 4.

By doing this, the video camera 4 performs a photographing operation in accordance with an input of the photographing instruction signal Pb. Therefore, a phase shift can be suppressed between the measurement sampling period Tb in the controller 6 and the photographing sampling period Ta in the video camera 4, and the reliability of an analysis result is improved.

In the high-speed tensile testing machine 1 according to the present embodiment, the video camera 4 generates one captured image E in synchronization with the photographing instruction signal Pb, every time the photographing instruction signal Pb is input.

By doing this, a captured image E without a phase shift from the measurement sampling period Tb of the controller 6 is obtained, and therefore an analysis result having higher reliability can be obtained.

In the high-speed tensile testing machine 1 according to the present embodiment, a measurement sampling period Tb according to impact speed can be set. Therefore, even in a case where a test is conducted at higher impact speed, a force detection signal D2 can be captured at a resolution sufficient with respect to a more abrupt change in a test piece TP, and a tensile force can be measured.

Second Embodiment

In the present embodiment, a case is exemplified where, from among high-speed video cameras, what is called an ultrahigh-speed video camera that has much higher photographing speed (frame rate) is used as the video camera 4.

The ultrahigh-speed camera is a camera that achieves photographing at an ultrahigh speed of at least one million frames/sec or more by using a sensor called a burst image sensor as an image sensor (an imaging element) and that generates a captured image group Eg including several tens to several hundred captured images E at a time in a single photographing operation.

In the present embodiment, "Hyper Vision HPV-X2" from Shimadzu Corporation serving as an ultrahigh-speed camera is used as the video camera 4, and this ultrahigh-speed camera generates a captured image group Eg of 256 captured images in a single photographing operation at a photographing speed of 10 million frames/sec. Stated another way, this ultrahigh-speed camera generates a captured image E in the order of approximately 0.1μseconds per image, and completes the generation of a captured image group Eg in a short time of approximately 25.6μseconds in a single photographing operation.

In this case, the video camera 4 performs a single photographing operation in synchronization with a measurement sampling period Tb, so that a phase shift can be suppressed to an almost negligible degree between each of the captured images E of a captured image group Eg obtained in the single photographing operation and the measurement sampling period Tb.

Figure 5:
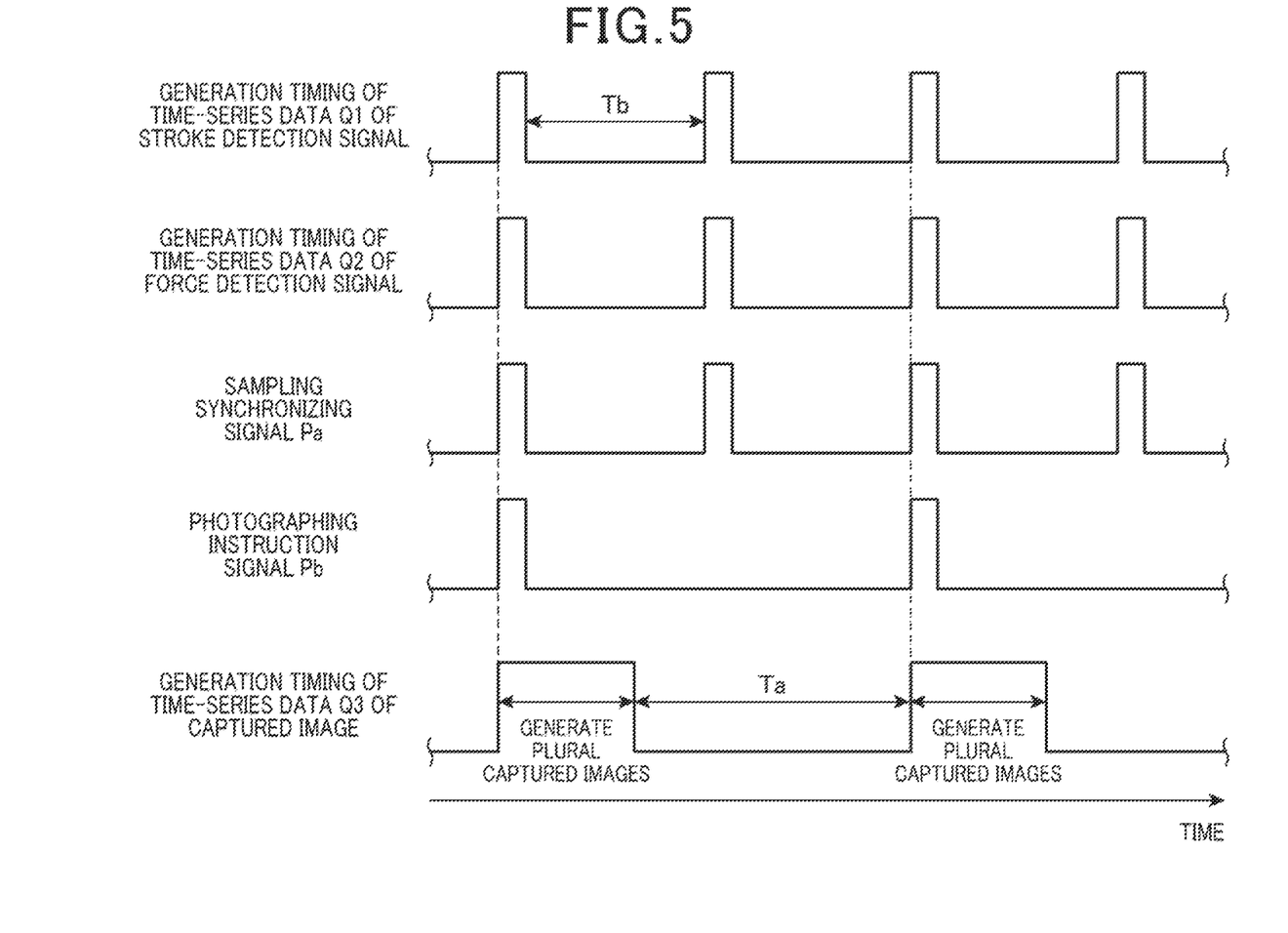
FIG. 5 is a timing chart according to a variation of the present invention.

Accordingly, in the present embodiment, as illustrated in FIG. 5, the video camera 4 performs a single photographing operation by using, as a trigger, an input of a photographing instruction signal Pb from the pulse generator 8 so as to generate a plurality of captured images E (in the present embodiment, 128 captured images) at high speed and generate a captured image group Eg.

By doing this, a first captured image E in each photographing operation is obtained in synchronization with a measurement sampling period Tb, and therefore this first captured image E can be used as an image that does not have a phase shift from the capturing of a force detection signal D2.

Further, a captured image group Eg obtained in a single photographing operation enables a deformation process of a test piece TP to be observed at shorter time intervals.

In each of the embodiments described above, one aspect of the present invention has been exemplified, and arbitrary modifications and applications can be made without departing from the gist of the present invention.

In each of the embodiments described above, the sampling synchronizing signal Pa or the photographing instruction signal Pb may be input to a variety of measurement instruments. This can suppress a phase shift from sampling periods of the variety of measurement instruments in addition to the measurement sampling period Tb and the photographing sampling period Ta, and a highly accurate test can be conducted. Examples of such a measurement instrument include a physical measurement instrument of temperature, pressure, or the like and an electric measurement instrument of an electric resistance, a voltage due to polarization, or the like.

A functional block illustrated in FIG. 2 is a schematic diagram illustrating components that have been classified according to the principal processing content, and the respective components can be classified into a larger number of components according to the processing content. In addition, a single component can be classified so as to perform a larger number of processes.

Further, in the embodiments described above, unless otherwise indicated, various numerical numbers do not intentionally exclude ranges around the various numerical numbers, but include the ranges around the various numerical numbers (what is called equivalents) in so far as the same effect is exhibited or critical significance exists.

Note that those skilled in the art could understand that a plurality of exemplary embodiments described above are specific examples of the following aspect.

(Paragraph 1) An impact testing machine in one aspect may include: a testing machine body that applies a load having a prescribed speed to a test piece and conducts a test; a controller that controls the testing machine body; a video camera that photographs the test piece; and a pulse generator. The controller may include: a detection signal capturing unit that captures a detection signal of the load in a measurement sampling period that has been prescribed; and a synchronizing signal output unit that outputs a sampling synchronizing signal that is synchronized with the measurement sampling period. The pulse generator may include: a photographing instruction signal generator that generates a photographing instruction signal by multiplying or dividing the sampling synchronizing signal, and outputs the photographing instruction signal to the video camera, the photographing instruction signal issuing a photographing instruction to the video camera.

According to Paragraph 1, the video camera performs a photographing operation in accordance with an input of the photographing instruction signal. Therefore, a phase shift between the measurement sampling period and a photographing sampling period of the video camera can be suppressed, and the reliability of an analysis result can be improved.

(Paragraph 2) In the impact testing machine described in Paragraph 1, the video camera may generate one captured image in synchronization with the photographing instruction signal, every time the photographing instruction signal is input.

According to Paragraph 2, a captured image without a phase shift from the measurement sampling period of the controller is obtained, and therefore an analysis result having higher reliability can be obtained.

(Paragraph 3) In the impact testing machine described in Paragraph 1 or 2, the video camera may be an ultrahigh-speed camera that generates a plurality of captured images in one photographing operation at a photographing speed of one million frames/sec or more. The video camera may perform the one photographing operation in synchronization with an input of the photographing instruction signal, and may generate the plurality of captured images.

According to Paragraph 3, a first captured image in each photographing operation is obtained in synchronization with the measurement sampling period. Therefore, this first captured image can be used as an image that does not have a phase shift from the capturing of a detection signal of the load.

Further, a plurality of captured images obtained in one photographing operation enable a deformation process of a test piece to be observed at shorter time intervals.

(Paragraph 4) In the impact testing machine described in any of Paragraphs 1 to 3, the setting of the measurement sampling period according to the speed of the load may be enabled.

According to Paragraph 4, even in a case where a test is conducted at higher speed, a detection signal can be captured at a resolution sufficient with respect to a more abrupt change in a test piece, and a load can be measured.

REFERENCE SIGNS LIST

1 High-speed tensile testing machine (impact testing machine)
2 Testing machine body
4 Video camera
6 Controller
7 Analysis device
8 Pulse generator
27 Load cell
33 Stroke sensor
52 Detection signal capturing unit
56 Synchronizing signal output unit
70 Photographing instruction signal generator
D1 Stroke detection signal
D2 Force detection signal
E Captured image
Eg Captured image group
Pa Sampling synchronizing signal
Pb Photographing instruction signal
TP Test piece
Ta Photographing sampling period
Tb Measurement sampling period

What is claimed is:

1. An impact testing machine comprising:
a testing machine body that applies a load having a prescribed speed to a test piece and conducts a test;
a controller that controls the testing machine body;
a video camera that photographs the test piece; and
a pulse generator, wherein
the controller includes:
a detection signal capturing unit that captures a detection signal of the load in a measurement sampling period that has been prescribed; and
a synchronizing signal output unit that outputs a sampling synchronizing signal that is synchronized with the measurement sampling period, and
the pulse generator includes:
a photographing instruction signal generator that generates a photographing instruction signal by multiplying or dividing the sampling synchronizing signal, and outputs the photographing instruction signal to the video camera, the photographing instruction signal issuing a photographing instruction to the video camera.

2. The impact testing machine according to claim 1, wherein
the video camera generates one captured image in synchronization with the photographing instruction signal, every time the photographing instruction signal is input.

3. The impact testing machine according to claim 1, wherein
the video camera includes an ultrahigh-speed camera that generates a plurality of captured images in one photographing operation at a photographing speed of one million frames/sec or more, and
the video camera performs the one photographing operation in synchronization with an input of the photographing instruction signal, and generates the plurality of captured images.

4. The impact testing machine according to claim 1, wherein
setting of the measurement sampling period according to a speed of the load is enabled.

* * * * *